United States Patent [19]
Horiguchi et al.

[11] Patent Number: 5,850,290
[45] Date of Patent: Dec. 15, 1998

[54] THREE-DIMENSIONAL SCANNER UTILIZING MOVING FRAME WITH DETECTORS

[75] Inventors: Chiyoharu Horiguchi; Shigeo Takahashi; Tetsuo Amano; Hiroyuki Matsuura; Koji Watase; Hideo Hiruma, all of Hamamatsu, Japan

[73] Assignee: Hamamatsu Photonics K.K., Hamamatsu, Japan

[21] Appl. No.: 919,332

[22] Filed: Aug. 28, 1997

[51] Int. Cl.⁶ .......................... G01B 11/14; G01B 11/24
[52] U.S. Cl. ............................................. 356/376; 356/375
[58] Field of Search .................................... 356/375–376

[56] References Cited

U.S. PATENT DOCUMENTS

| | | | |
|---|---|---|---|
| 4,406,544 | 9/1983 | Takada et al. | 356/376 |
| 4,679,076 | 7/1987 | Vikterlof et al. | 356/376 |
| 4,786,925 | 11/1988 | Landwehr | 356/376 |
| 5,477,371 | 12/1995 | Shafir | 356/376 |
| 5,636,030 | 6/1997 | Limbach | 356/376 |
| 5,666,957 | 9/1997 | Juto | 356/375 |

FOREIGN PATENT DOCUMENTS

| | | |
|---|---|---|
| 0 305 107 | 3/1989 | European Pat. Off. |
| 1-121707 | 5/1989 | Japan |
| 5-71882 | 5/1989 | Japan |
| 2 069 690 | 8/1981 | United Kingdom |

Primary Examiner—Frank G. Font
Assistant Examiner—Jason D. Vierra-Eisenberg
Attorney, Agent, or Firm—Pillsbury Madison & Sutro LLP

[57] ABSTRACT

A three-dimensional shape measuring apparatus includes a moving frame arranged to surround a measurement space. The moving frame is arranged to be movable in a vertical direction. A plurality of sensors is disposed opposite to each other on two opposite sides of the moving frame and are arranged to effect a horizontal scanning of light to measure distances to a human body being measured. A driving mechanism moves the moving frame. An analyzer calculates distances to the human body, based on output signals from respective sensors, to analyze data of a surface position of the human body, i.e., a three-dimensional shape thereof. The apparatus further includes a placement state on which the human body is placed. Since the sensors are located so as to face the front and the back of the human body, the apparatus can also measure portions below an armpit and below a crotch.

20 Claims, 13 Drawing Sheets

LONGITUDINAL, CROSS-SECTIONAL VIEW

CROSS-SECTIONAL VIEW OF
DISTANCE MEASURING RING

THREE-DIMENSIONAL SCANNER UTILIZING MOVING FRAME WITH DETECTORS

BACKGROUND OF THE INVENTION

1. Field of the Invention

The present invention relates to a three-dimensional shape measuring apparatus for measuring a three-dimensional shape of a surface of a body to be measured, such as the human body.

2. Related Background Art

A conventionally known three-dimensional shape measuring apparatus is the one described in the bulletin of Japanese Patent Publication No. Hei 5-71882. This three-dimensional shape measuring apparatus is so constructed, as shown in FIGS. 13A and 13B, as to have a distance measuring ring 120 in which a plurality of detection heads 121 for detecting distances to the surface of measured object 2 are arranged circumferentially and the whole of which is arranged as vertically movable, a guide member 102 for guiding the vertical movement of the measuring ring 120, and a driving mechanism 103 for moving this measuring ring 120. With this three-dimensional shape measuring apparatus, the measured object 2 such as the human body is located in the measuring ring 120, the measuring ring 120 is moved up and down while operating the detection heads 121, distance data of each detection head 121 is collected at each vertical position of the measurement ring 120, and the data is processed, thus measuring the three-dimensional shape of the surface of the measured object 2. Since the measuring ring 120 is heavy, this three-dimensional shape measuring apparatus requires some time before moving velocity becomes uniform, because of inertia. For also carrying out accurate shape measuring during that period, positions of the measuring ring 120 are detected and the operation timing of the measuring ring 120 is matched with that of the detection heads 121, whereby the shape of the measured object 2 can be measured accurately.

This conventional three-dimensional shape measuring apparatus, however, has various problems listed below.

First, many detection heads 121 are necessary for accurately measuring the surface shape of the measured object. This increases the cost. Further, they must be located accurately toward a predetermined point (toward the center), which makes adjustment difficult. This required a time-consuming adjustment by an engineer after installation, which increased introduction cost.

Second, since each detection head 121 (distance sensor) installed in the measuring ring 120 is directed toward the center of the measuring ring 120, when the surface of the measured object 2 has projections and depressions, accurate measurement of the projected or depressed portions cannot be performed. For example, when the measured object is the human body, portions below the armpit part and below the crotch between two legs, which are recessed portions, are interrupted by other parts of the measured body itself, for example, by the arm or the thigh, which does not allow accurate measurement of the shape of the projected or depressed portions.

Third, when the measured object is one having heavy weight, such as the human body, and when the measured object is located in the apparatus for measurement, there could occur a case wherein the apparatus is distorted finely by the weight of the measured object. In that case deviation occurs between relative positions of the measuring ring and the measured object, which does not allow accurate measurement. In order to solve such a problem, it is conceivable to construct the apparatus in a structure with enhanced rigidity by strengthening the frame of the apparatus. This structure, however, increases the weight of the entire apparatus greatly, which makes the assembling and installation of the apparatus difficult, thus degrading handlability. In addition, the apparatus cannot be installed at places except where a floor can support the weight, consequently, places at which the apparatus can be installed are limited. Further, this causes the cost of parts of the apparatus to be increased.

Fourth, measurement is limited only to objects smaller than the movable range of the measuring ring. Specifically, when the measured object is a tall object higher than the movable range of the measuring ring, the shape of the measured object can be measured naturally only in the movable range of the measuring ring. Namely, there are cases wherein shapes of the upper and lower parts of the measured object cannot be measured.

Fifth, if the measured object set in the apparatus for measurement moves during measurement, the measurement will be invalidated and the measured object could touch the measuring ring causing the measuring ring to be damaged or broken.

Sixth, since the measuring ring is heavy, a large-scale motor needs to be mounted, as a driving means, for driving the measuring ring, which further increases the weight of the entire apparatus and which also increases the power necessary for operating the motor.

The present invention solves the above problems.

A first object of the present invention is to provide an apparatus capable of accurately measuring a three-dimensional shape using a small number of sensors.

A second object of the present invention is to provide a three-dimensional shape measuring apparatus capable of accurately measuring the shape of the portions below the armpit, and below the crotch, between the two legs, when the measured object is the human body.

A third object of the present invention is to provide a light-weight apparatus capable of measuring a heavy object.

A fourth object of the present invention is to provide an apparatus capable of accurately measuring a whole large-scale measured object.

A fifth object of the present invention is to provide an apparatus that assures protection of the sensors and provides security of the measured object.

Finally, a sixth object of the present invention is to decrease operation power of apparatus.

SUMMARY OF THE INVENTION

The present invention is a three-dimensional shape measuring apparatus for detecting a three-dimensional shape of a measured object placed in a measurement space in a non-contact manner, comprising: (1) a moving frame disposed around the measurement space so as to surround a predetermined axis passing through a center of the measurement space and arranged as movable in a direction of the axis; (2) four or more sensors for measuring distances to surfaces of different portions of the measured object, the sensors being positioned along a circumferential direction on the moving frame so that plural sensors are located mainly in each of predetermined regions on two opposite sides of the moving frame; (3) a driving mechanism for moving the moving frame in the direction of the axis; (4) position detecting means for detecting and outputting a position of the moving frame in the direction of the axis; and (5) analyzing means for calculating data reporting a distance from each sensor to a surface of the measured object at each moving position of the moving frame, based on outputs from each sensor and the position detecting means, and for analyzing a three-dimensional shape of the surface of the measured object, based on the data of distance.

In this apparatus, the measured object is placed in the measurement space, and distances between the surface of the measured object and the sensors are measured by the plural sensors disposed on the moving frame while moving the moving frame in the direction of the predetermined axis. These sensors are positioned as concentrated in the predetermined regions on opposite sides with respect to the measurement space. Accordingly, the sensors disposed on one side are arranged opposite to the sensors disposed on the other side. In the case wherein the surface of the measured object has projections and depressions, the measurement is carried out with the projected or depressed surface being opposed to either sensor, which achieves sure distance measurement to the projected or depressed surface. During the distance measurement by the sensors, positions of the moving frame upon the distance measurement are also measured by the position detecting means. Position data indicating three-dimensional coordinates of the positions of the respective sensors, during the distance measurement, is obtained from the positions of the moving frame. Obtained from this position data and the distance data between the sensors and the surface of the measured object, detected during movement of the moving frame, is the position data indicating the three-dimensional coordinates of positions of the surface of the measured object in the measurement space. This position data is three-dimensional data indicating the shape of the surface of the measured object. The three-dimensional shape of the surface of the object having projections and depressions can be measured accurately in this way.

In an alternative arrangement, a three-dimensional shape measuring apparatus according to the present invention may be arranged to comprise, instead of (2) discussed above, (2a) a plurality of sensors disposed along a circumferential direction on the moving frame, for measuring distances to surfaces of different portions of the measured object and characterized in that optic axes of the respective sensors do not intersect at one point on a projection surface in the direction of the axis.

Since this apparatus is arranged so that orientations of the sensors are so different as to prevent all the sensors from being directed to a specific point in the measurement space (or to a specific straight line parallel to the above direction of the axis where the sensors are positioned at different positions in the direction of the axis), even if the surface of the measured object has projections and depressions, the distance measurement to the projected or depressed surface can be carried out accurately by placing the measured object so that the projected or depressed surface is directed toward either sensor. The three-dimensional shape of the surface of the object can also be measured accurately in this case.

Further, the apparatus may be arranged in such a manner that the sensors detect distances to the measured object by triangulation, each sensor having a light projecting portion for projecting light toward the measured object and a light receiving portion, disposed a predetermined distance apart from the light projecting portion, for receiving scattered or reflected light from the measured object, wherein the light projecting portion effects scanning of light within a predetermined angle in a direction perpendicular to the direction of the axis.

This arrangement causes the light projected from the light projecting portion to be irregularly reflected (scattered) on the surface of the measured object and part of the reflected light is incident to the light receiving portion disposed at the position being the predetermined distance apart from the light projecting portion. A triangular shape is formed by paths of the light traveling from the light projecting portion via the surface of the measured object to the light receiving portion and the triangular shape differs depending upon the position on the measured object. As a result, an angle or a position of incidence of the reflected light entering the light receiving portion differs, based on which a distance to the surface of the measured object can be obtained by triangulation. Further, scanning of light perpendicular to the axial direction enables one sensor to measure distance data corresponding to a plurality of different surface positions on the measured object. Namely, it permits accurate measurement by a small number of sensors, which simplifies adjustment and decreases the manufacturing costs and the costs of adjustment or the like upon installation.

The apparatus may also be arranged in such a way that scanning centers of the respective light projecting portions in the sensors disposed adjacent to each other on a same side of the moving frame intersecting with each other more distant from the sensors than the center of the measurement space.

Since this arrangement locates each sensor more opposite to the opposed sensor, in the case wherein the surface of the measured object has projections and depressions, the measurement is carried out with the projected or depressed surface being directed to either one of the sensors, which further facilitates incidence of light from the light projecting portion to the depressed surface and which makes it easier for the light receiving portion to receive the scattered light. Therefore, the measurement can be carried out with reliability, for example, for the shapes of the portions below the armpit and below the crotch of the human body.

The apparatus may be arranged in such a way that the light receiving portion of each sensor is disposed a predetermined distance apart in the direction of the axis from the light projecting portions of the other sensors disposed opposite thereto. This arrangement prevents the irradiation light from the light projecting portions from directly entering the light receiving portions of the respective sensors even in the case wherein the measured object does not interrupt the space between the light receiving portion of each sensor and the light projecting portions of the sensors disposed opposite thereto. Namely, high accuracy measurement with less noise can be achieved.

The moving frame may be of a U-shape or horseshoe shape. In this case, one side of the moving frame is opened and the opening portion can be utilized for introduction of the measured object or the like.

The apparatus may further comprise a placement stage, on which the measured object is placed, in the measurement space. This arrangement enables the measurement down to the lowermost part of the measured object. Detachable arrangement of this placement stage allows sure measurement of the total three-dimensional shape even of a tall measured object.

The apparatus may further comprise an internal wall cover for separating the measurement space from a moving space of the moving frame. This arrangement surely separates the measurement space from the moving space of the moving frame, thereby assuring safe measurement.

The apparatus may further comprise an internal wall cover for separating the measurement space from the moving space of the moving frame, the internal wall cover having windows for transmitting light in portions between the sensors and the measured object. This arrangement separates the measurement space from the moving space of the moving frame and prevents input/output light of the sensor from being interrupted. Accordingly, the arrangement assures safe and accurate measurement.

The apparatus may be arranged in such a manner that the direction of the axis is substantially the direction of gravity, the three-dimensional shape measuring apparatus further comprising a rotating member disposed above the measurement space, and a flexible elongate member connected at one end thereof to the moving frame and at the other end thereof to a balancer having substantially the same weight as the moving frame, the flexible elongate member being hooked around the rotating member, wherein the driving mechanism rotates the rotating member to move the moving frame through the flexible elongate member.

This arrangement substantially balances the moving frame with the balancer connected to the flexible elongate member, which decreases the force necessary for rotating the rotating member for moving the moving frame. This enhances movement efficiency of the moving frame and decreases the consumption power of the apparatus.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

Figure 1:
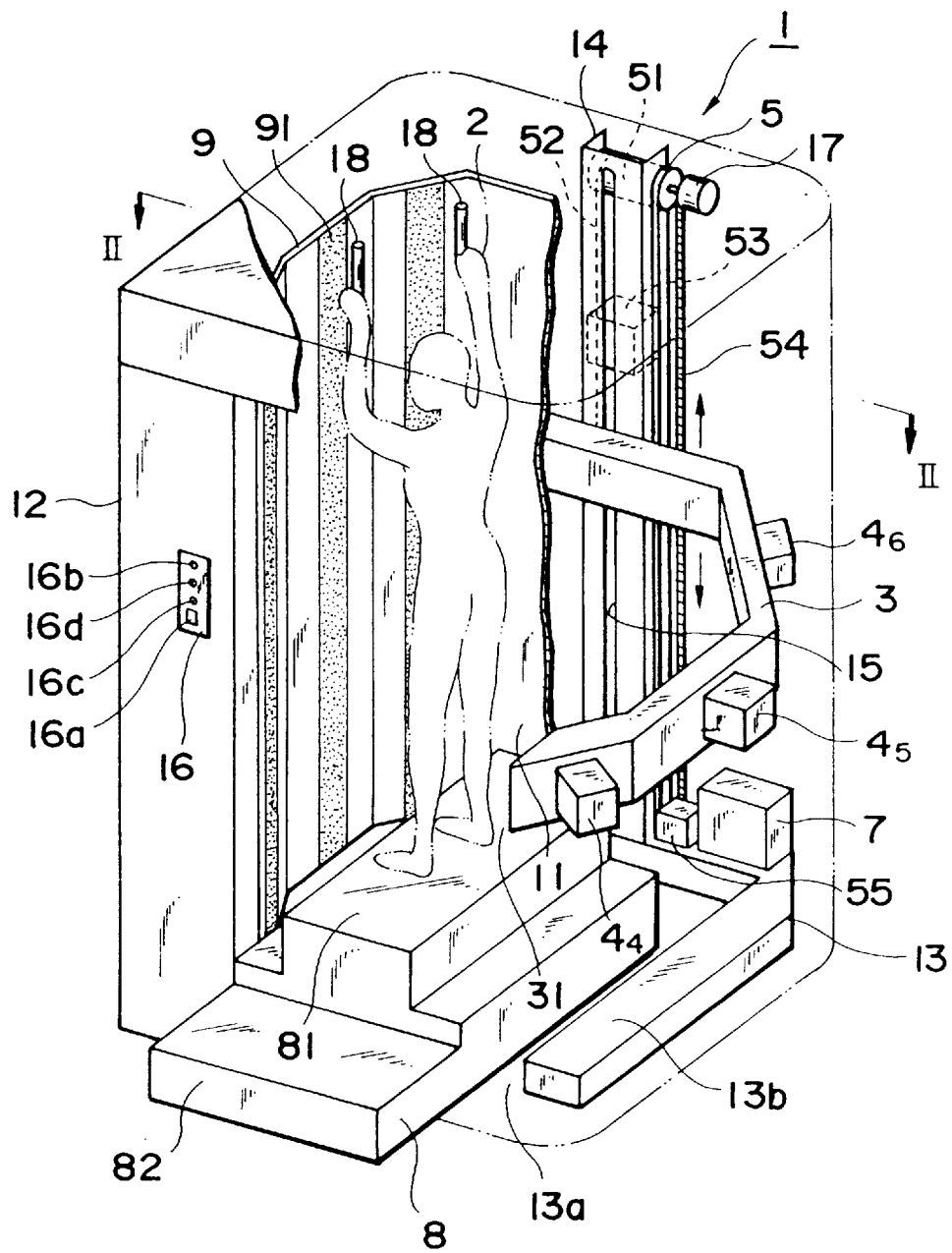
FIG. 1 is a total, schematic drawing of a three-dimensional shape measuring apparatus according to an embodiment of the present invention.

Embodiments of the three-dimensional shape measuring apparatus according to the present invention will be described based on the accompanying drawings. In the drawings the same elements will be denoted by the same symbols and redundant description will be omitted. It is also noted that dimensions and ratios of the drawings do not always coincide with those in the description.

Figure 2:
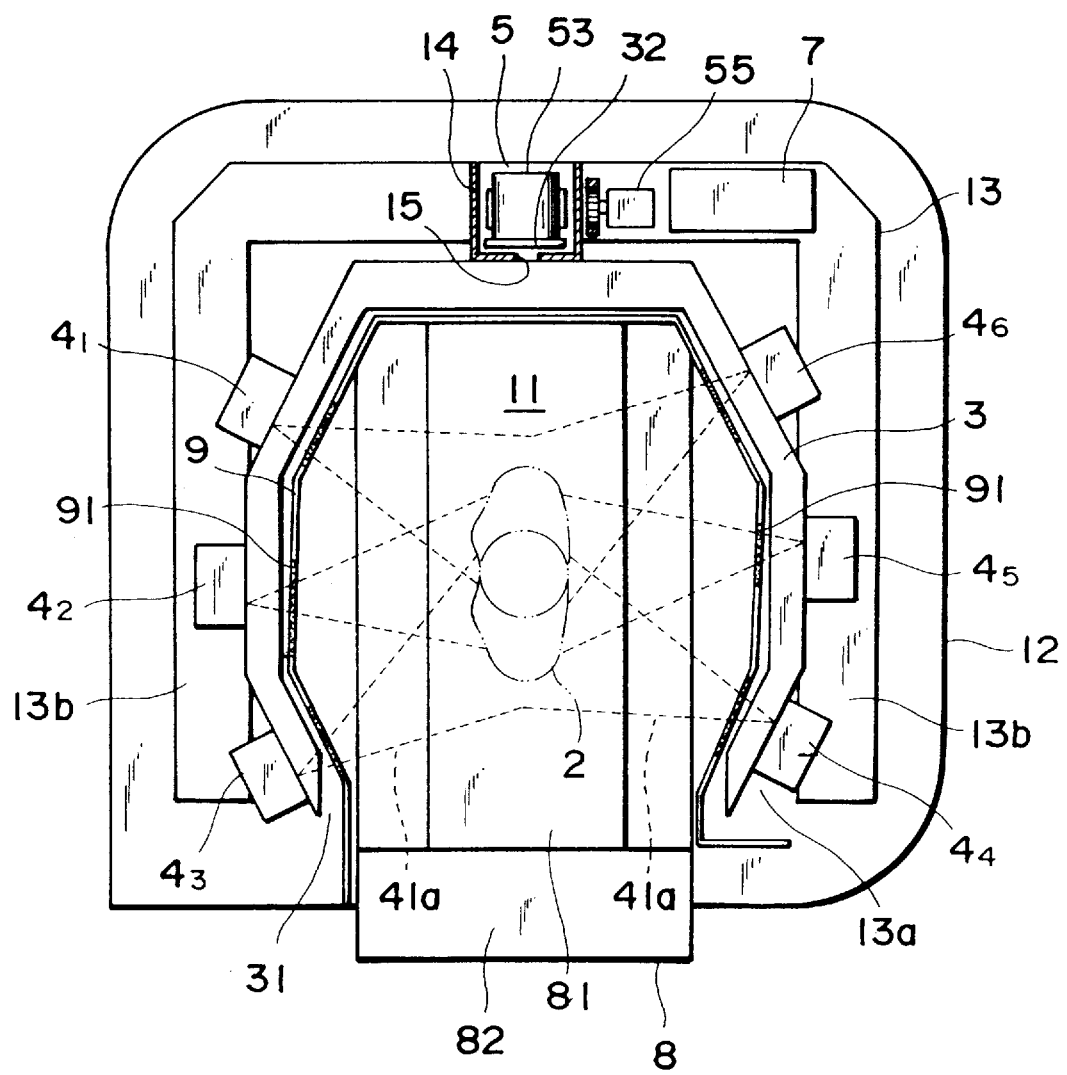
FIG. 2 is a cross-sectional view along II—II line of FIG. 1.

FIG. 1 is a total, schematic drawing of the three-dimensional shape measuring apparatus 1 in an embodiment of the present invention and FIG. 2 is a horizontal, cross-sectional view of the three-dimensional shape measuring apparatus 1. As shown in FIG. 1, the three-dimensional shape measuring apparatus 1 according to the present embodiment is an apparatus for measuring the shape of the human body (the contour of the body, a partial configuration of the body, etc.) when the human body 2 is a measured object. Inside the apparatus a measurement space 11 is formed and a moving frame 3 is arranged to be vertically movable along the measurement space 11. The moving frame 3 is for successively measuring the shape of the human body 2 along the vertical direction and a plurality of sensors 4 are installed thereon along the circumferential direction of the moving frame 3. The shape of this moving frame 3 is one capable of surrounding the measurement space 11, which is, for example, a horseshoe shape as shown in FIG. 2. Namely, when the moving frame 3 is formed in the horseshoe shape to provide a cutout portion 31 in a part of the moving frame 3, a man can always go into or out of the measurement space 11 wherever the moving frame 3 is located, despite the form surrounding the measurement space 11.

The sensors 4 are for detecting distances to the human body 2 located in the measurement space it and are positioned so as to be capable of detecting distances to different positions on the surface along different directions to the human body 2. In FIG. 2, the moving frame 3 is provided with six sensors $4_1$ to $4_6$, but the number of set sensors 4 may be seven or more or five or less, if the shape can be measured throughout the overall periphery of the human body 2. It is, however, clear that at least three sensors 4 are necessary for accurately measuring the shape of the overall periphery of human body 2, and preferably, four or more sensors 4 are positioned for accurately measuring the shape of the overall periphery.

The sensors 4 are arranged as divided into two sets ($4_1$ to $4_3$ and $4_4$ to $4_6$), each including three, on opposite side faces of the horseshoe-shaped moving frame 3. The details of locations of sensors 4 will be described hereinafter, and the structure of individual sensors is described first. These sensors 4 may be, for example, reflection-type photoelectric sensors for detecting distance by optical triangulation.

Figure 3:
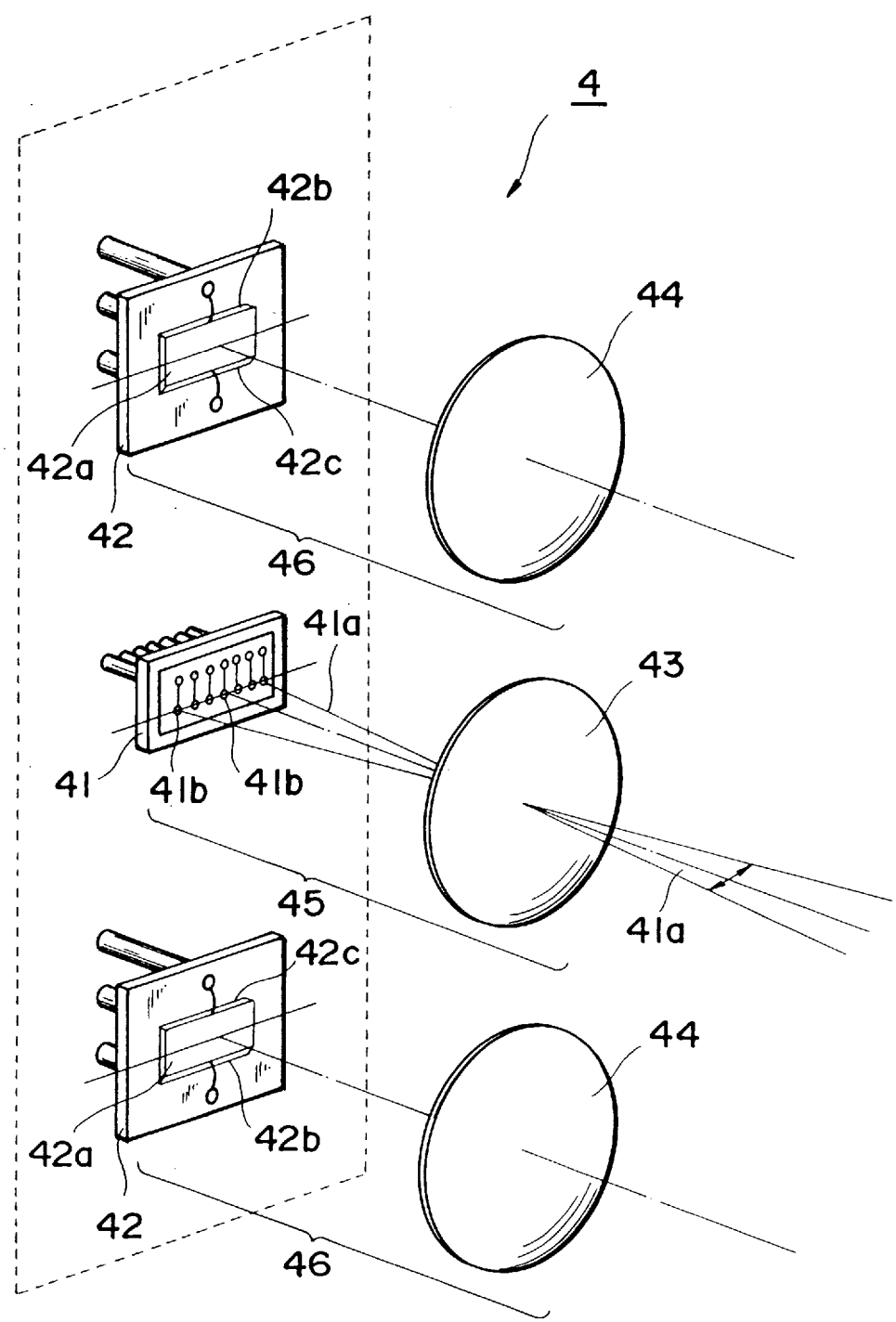
FIG. 3 is a schematic, perspective view to show the arrangement of the sensor in the apparatus of FIG. 1.

For example, a sensor 4 has a light projecting portion 45 and two light receiving portions 46 located above and below in symmetry on either side of the light projecting portion 45, as shown in FIG. 3. In the light projecting portion 45, light projection lens 43 for changing irradiation light into parallel light is located in front of light emitting portion 41 and this light emitting portion 41 has a plurality of light emitting elements 41b composed of LED chips arrayed in line in the horizontal direction. These light emitting elements 41b are controlled to emit light in order, whereby beams 41a emitted therefrom and traveling toward the human body 2 experience fan-shaped scanning out of the light projection lens 43. This horizontal scanning of beams 41a expands the irradiation area of beams 41a in one sensor 4, i.e., the distance-detectable range by the sensor 4, which allows the number of set sensors 4 to be decreased.

On the other hand, each of the light receiving portions 46 has a light receiving element 42 and a light reception lens 44, disposed in front thereof, for receiving reflected light and condensing the light on the surface of light receiving element 42. This light receiving element 42 is, for example, a PSD (position sensitive device). Specifically, the light receiving element 42 has a light receiving surface 42a comprised of a resistor layer and is constructed to have electrodes 42b, 42c disposed at the upper and lower edges of the light receiving surface 42a on either side thereof. This light receiving element 42 is arranged so that when light is incident to the light receiving surface 42a, photocurrent occurs at a light receiving position and this photocurrent is divided into two currents, which flow to the respective electrodes 42b, 42c. On that occasion, the photocurrent is divided into two currents flowing toward the respective electrodes 42b, 42c according to resistances between the light receiving position and each electrode 42b, 42c. Accordingly, ratios of the electric currents flowing to the respective electrodes 42b, 42c change according to light receiving positions of incident light to the light receiving element, which allows detection of the light receiving position.

The light projecting portion 45 and light receiving portions 46 are positioned so that the centers of their optic axes may become coincident with each other. Namely, the light emitting portion 41 and the light receiving elements 42, and the light projection lens 43 and light reception lenses 44 each are arranged in parallel.

Figure 4:
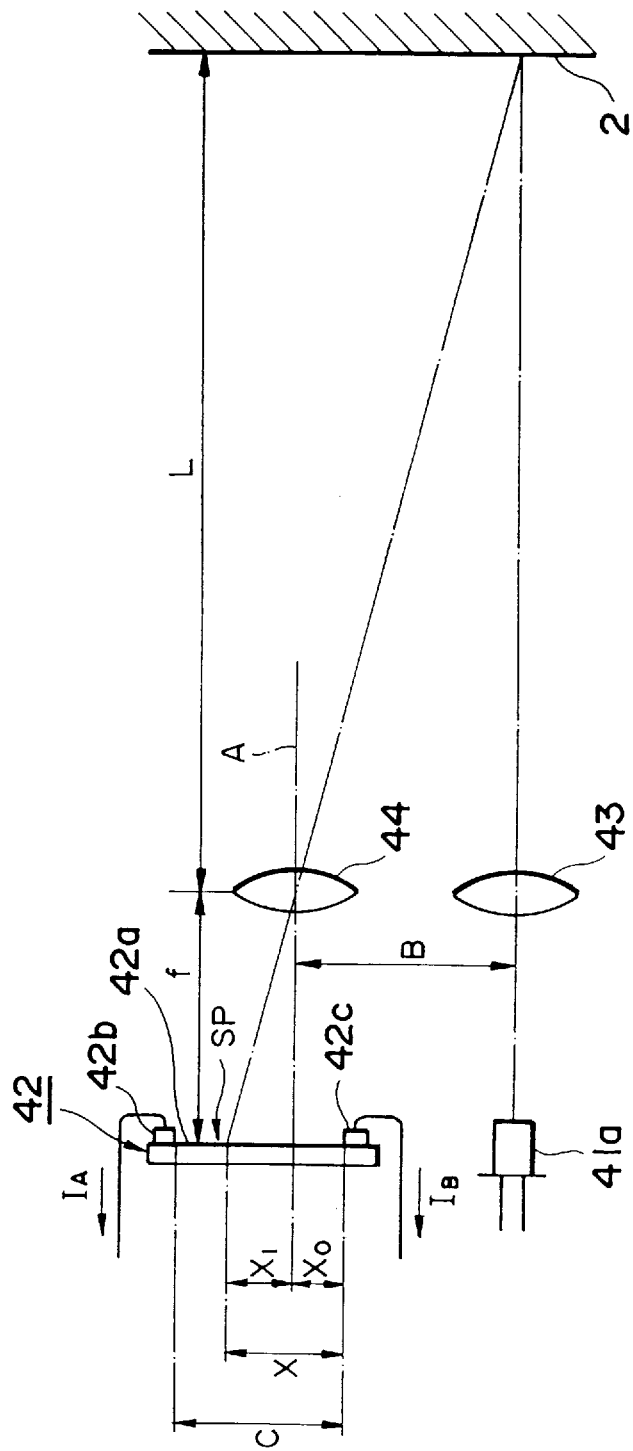
FIG. 4 is an explanatory drawing to show the measurement principle of the sensor of FIG. 3.

Now, the measurement principle of this sensor 4 will be described briefly. FIG. 4 is a drawing to show the measurement principle of this sensor. The light launched from LED chip 41a travels through the light projection lens 43 to be irregularly reflected by the surface of human body 2, being the measured object, and part thereof is collected by the light reception lens 44 to be incident to a light receiving position SP on the light receiving surface 42a of the light receiving element 42. Here, let L be a distance from the light projection lens 43 to the human body 2, B be a base length which is a distance between the centers of the optic axes of the light projection lens 43 and light reception lens 44, f be a focal length of the light reception lens 44, i.e., a distance between the light reception lens 44 and the light receiving element 42, C be a distance between the electrodes 42b, 42c, and $x_1$ be a distance of the light receiving position SP from the center of the optic axis of the light reception lens 44. Then the following equation holds.

$$x_1 = Bf/L \quad (1)$$

Further, let $I_0$ be the sum of output currents $I_A$, $I_B$ from the respective electrodes 42b, 42c of the light receiving element 42. Since the output currents $I_A$, $I_B$ are in inverse proportion to the distance between the light receiving position SP and each electrode, the output currents $I_A$, $I_B$ can be expressed by the following equations, where X is the distance between the light receiving position SP and the electrode 42c.

$$I_A = I_0 X/C$$

$$I_B = I_0(C-X)/C \quad (2)$$

and $$X = i_0 + x_1 \quad (3)$$

where $x_0$ is the distance between the center of the optic axis of the light reception lens 44 and the electrode 42c. To eliminate X and $x_1$ from Eqs. (1) to (3), the following equation holds.

$$L = Bf / \left( \frac{I_A}{I_A + I_B} C - x_0 \right) \quad (3a)$$

Therefore, the distance L to the human body 2, being the measured object, can be obtained from the currents $I_A$ and $I_B$.

Figure 5:
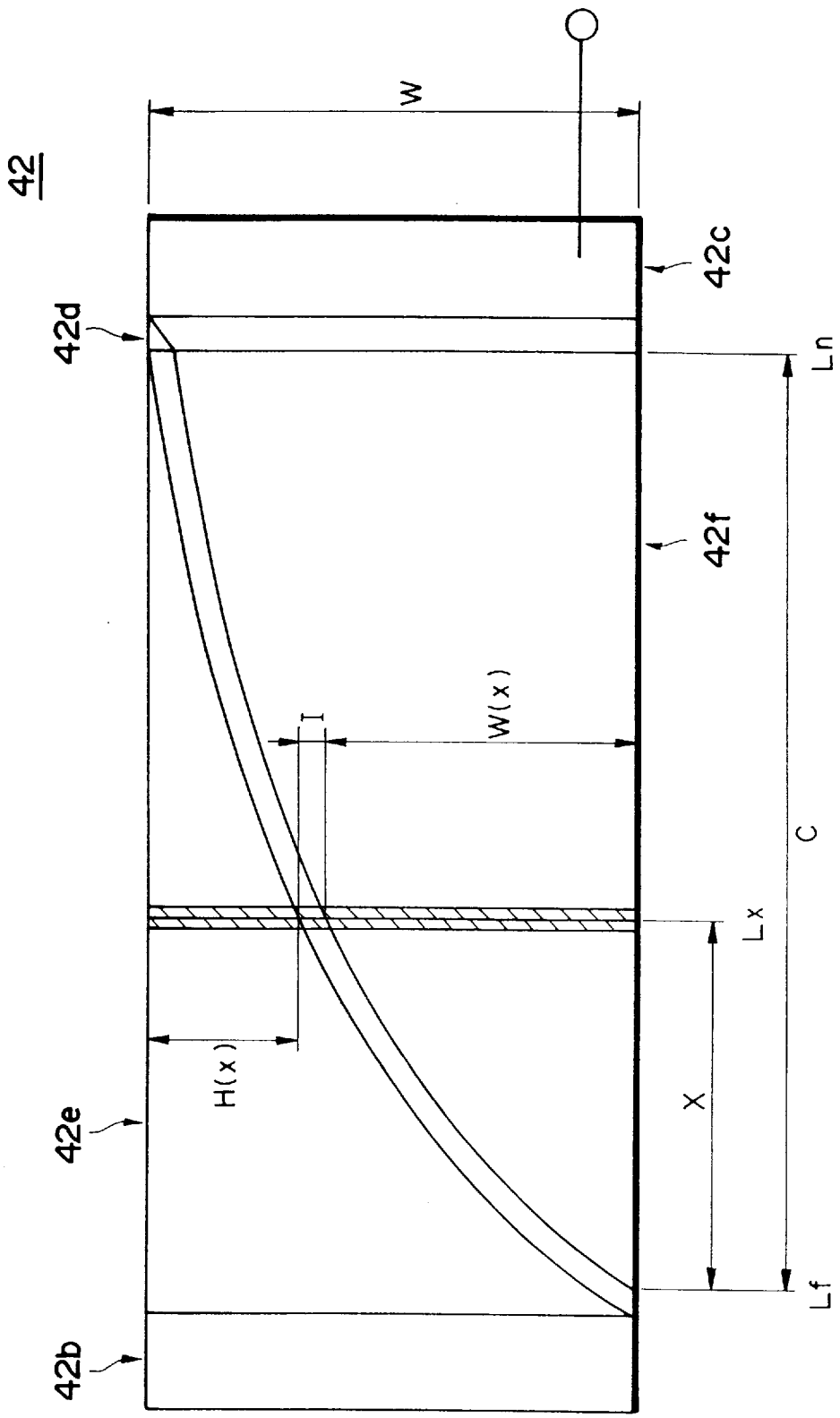
FIG. 5 is a drawing to show another embodiment of a light receiving element of the sensor associated with FIG. 2.

In an alternative arrangement, the light receiving element 42 may be a two-segment-type position sensitive device as shown in FIG. 5. In this two-segment-type position sensitive device, a separating layer 42d of a predetermined curve shape insulatively separates the light receiving surface 42a into two light receiving faces 42e, 42f. Each light receiving face is provided with an electrode 42b, 42c. In this case, when slit light parallel to the electrodes 42b, 42c is incident to the light receiving surface 42a, electric currents are taken out of the respective electrodes in accordance with areas on the respective sides of the light receiving faces. Accordingly, the light receiving element 42 that obtains linear output to the distance L described above can be fabricated by adjusting the shape of this curve.

Conditions to be satisfied by the shape of the separating portion 42d of the light receiving element 42 capable of obtaining the linear output to the distance L as described above are as follows:

$$H(x) + W(x) + I = W$$

$$W(x) = ax/(x+b) \quad (4)$$

where H(x) is a width of the light-source-side light receiving face at position x from the light source, W(x) is a width of the opposite-side light receiving face, I is a width of the separating layer, and W is a width of the total light receiving surface; and constants a, b satisfy the following conditions.

$$a = L_f(W-1)/(L-L_n)$$

$$b = fB/L_f \quad (5)$$

where $L_f$ and $L_n$ represent measurement limits on the far distance side and on the near distance side, respectively.

As described previously, the light emitting portion 41 includes the light emitting elements 41b arranged horizontally in line, and successive light emission of these light emitting elements achieves horizontal scanning of beams 41a irradiating the human body 2 from the light projection lens 43. By detecting scattered light of each beam by the light receiving element 42, the distance to the human body 2, being the measured object, can be measured based on the aforementioned principle. A horizontal incidence position of reflected light of the scan light to the light receiving surface 42a of the light receiving element 42 is equal to a horizontal position of light emitting element 41b having emitted the scan light. Therefore, the horizontal width of the light receiving element 42 needs to be greater than the horizontal array length of the light emitting elements 41b.

Since the sensor 4 is arranged so that the light receiving elements 42 are located above and below in symmetry on either side of the light emitting portion 41 as shown in FIG. 3, even if the surface of human body 2 has projections and depressions changing perpendicularly thereto, either one of the upper and lower light receiving elements 42 can receive scattered light of beam 41a irradiating the surface of human body 2, whereby surface positions of such projections and depressions can be measured for certain.

Figure 6:
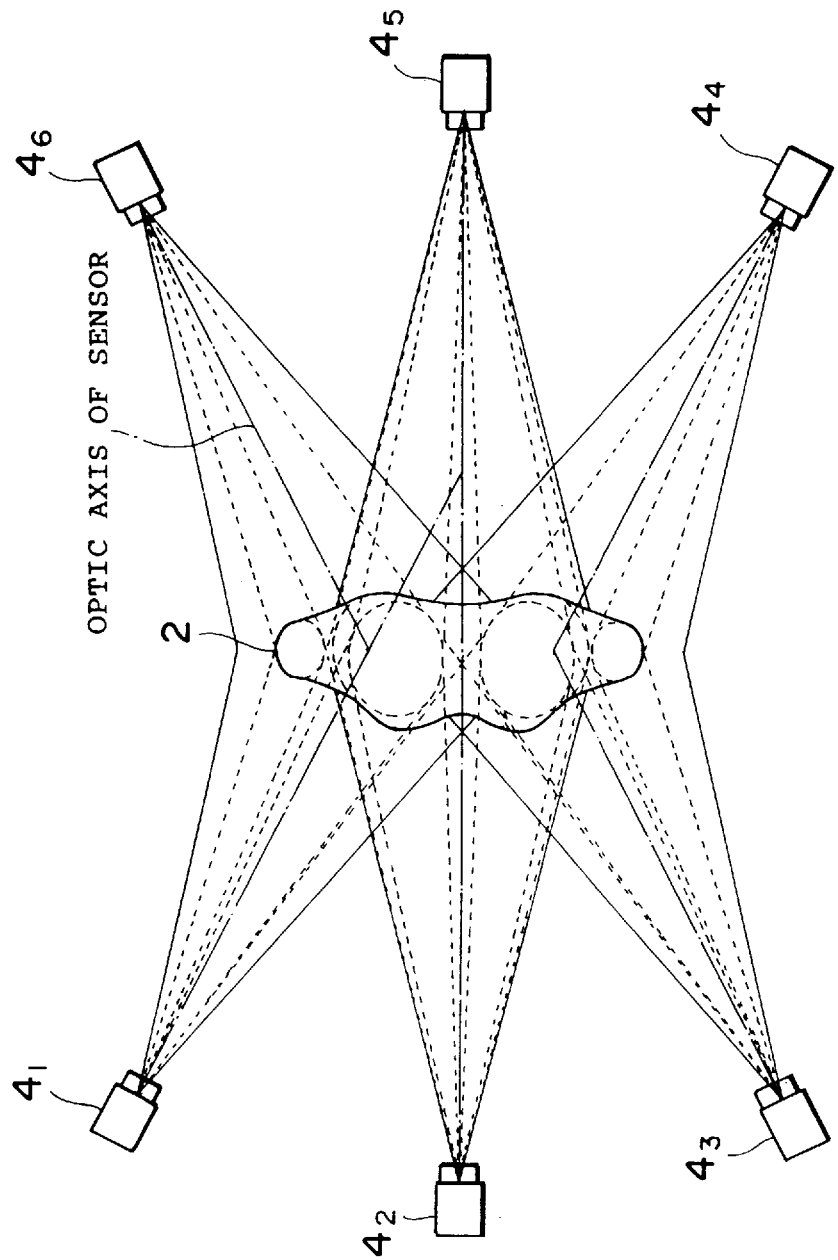
FIG. 6 is a schematic, lateral, cross-sectional view of the three-dimensional shape measuring apparatus of FIG. 1.

Next, the arrangement of the group of sensors 4 will be described. The detailed arrangement of sensors 4 is shown in FIG. 6. In the case of the present embodiment, the sensors 4 are arranged in symmetry in front of and behind the human body 2 with respect to the center of the measurement space. On either side, three sensors are arranged equally in an angular range of about 70° around the center of the measurement space. The optic axes (the center axes of horizontal scan) of the sensors $4_1$ to $4_3$ (or $4_4$ to $4_6$) intersect 200 mm away from the center of the measurement space. Namely, the sensors are located as concentrated with each sensor being opposed to the front or the back of the human body 2. Each of these sensors 4 has a horizontal scan angle of about 30°. Therefore, scanning ranges of the respective sensors 4 overlap with each other, so that the portions below the armpit part and below the crotch part, which are likely to be interrupted by the measured object itself upon measurement so as to become out of sight, can be measured accurately, because they are on lines of sight of either sensor 4.

Further, each light receiving portion 46 in the sensor group $4_1$ to $4_3$ mounted on one side of the moving frame 3 is installed preferably at a height different from those of the light projecting portions 45 of the sensor group $4_4$ to $4_6$ mounted on the other side, more preferably at a height apart by the diameter of light projection lens 43 (or light reception lens 44) or more. This prevents the light emitted from the light projection portion 45 of each sensor 4 on one side and the scattered light from entering the light receiving portions 46 of the sensors 4 mounted on the opposite side, which can prevent generation of noise due to incidence of unwanted light.

Returning to FIG. 1, the description of the whole of the present embodiment will be continued. The moving frame 3 is arranged to be movable in the vertical direction by means of a driving mechanism 5. This driving mechanism 5 is arranged so that a wire 52 being a flexible elongated body is hooked around a roller 51, which is a rotating member arranged to be rotatable. Thewire 52 is coupled at one end with the moving frame 3 and at the other end with a balancer 53 of a metal body or the like having a weight being nearly equal to that of the moving frame 3. The roller 51 is horizontally journaled in the upper part of column 14 standing on base plate 13. This roller 51 is arranged in a structure such that a rotating force of motor 55 is transmitted through a belt 54 thereto to rotate according to a drive of motor 55. Since the balancer 53 and moving frame 3 are suspended by the wire 52 and are almost balanced, the power needed for moving the moving frame 3 is small and the movement of the moving frame 3 is smooth. Owing to this, a small-torque motor can be applied as the motor 55 used for driving the moving frame 3, so that the necessary power can be decreased upon operation of apparatus 1.

The base plate 13 is a generally U-shaped plate member, which is placed on a floor surface in an outer wall portion 12 of the apparatus 1. The base plate 13 is placed so that an opening portion thereof 13a is directed toward the exit/entrance of the measurement space 11 for the human body 2, similar to the cutout portion 31 of the moving frame 3. Column 14 stands in the central portion of the base plate 13 and has such a structure that a slit 15 is formed along the vertical direction, i.e., along the moving direction of the moving frame 3 in a surface facing the measurement space 11. The slit 15 is a guide hole for guiding the moving frame 3 and an engagement piece 32 of the moving frame 3 is engaged in this slit 15, whereby the moving frame 3 can slide only in the aperture direction (along the longitudinal direction) of this slit 15. Although FIG. 1 illustrates only the column 14 standing from the base plate 13, a desired arrangement is such that an auxiliary column, in addition to the column 14, is provided so as to stand vertically on the base plate 13 and that a horizontal member connects the upper parts of the column 14 and auxiliary column with each other to enhance the rigidity of apparatus 1. The moving frame 3 may be engaged to a slider portion which is comprised of a guiding rail and a slider without using slit 15.

A control panel 16 is attached to the outer wall portion 2 and is provided with main power switch 16a for switching of power supply/interruption to the apparatus 1, start/stop switch 16b for starting or stopping the measurement, error display LED 16c for indicating an abnormal operation, and set switch 16d for setting the apparatus 1 in a measurement state. The driving mechanism 5 is provided with a rotary encoder 17 for outputting a pulse signal according to an amount of movement of the moving frame 3. The rotary encoder 17 is, for example, one having a rotating member arranged to rotate in synchronism with the rotary axis of roller 51. This rotary encoder 17 can detect the rotating status of roller 51 to output a pulse signal synchronous with an amount of movement of the moving frame 3.

Figure 7:
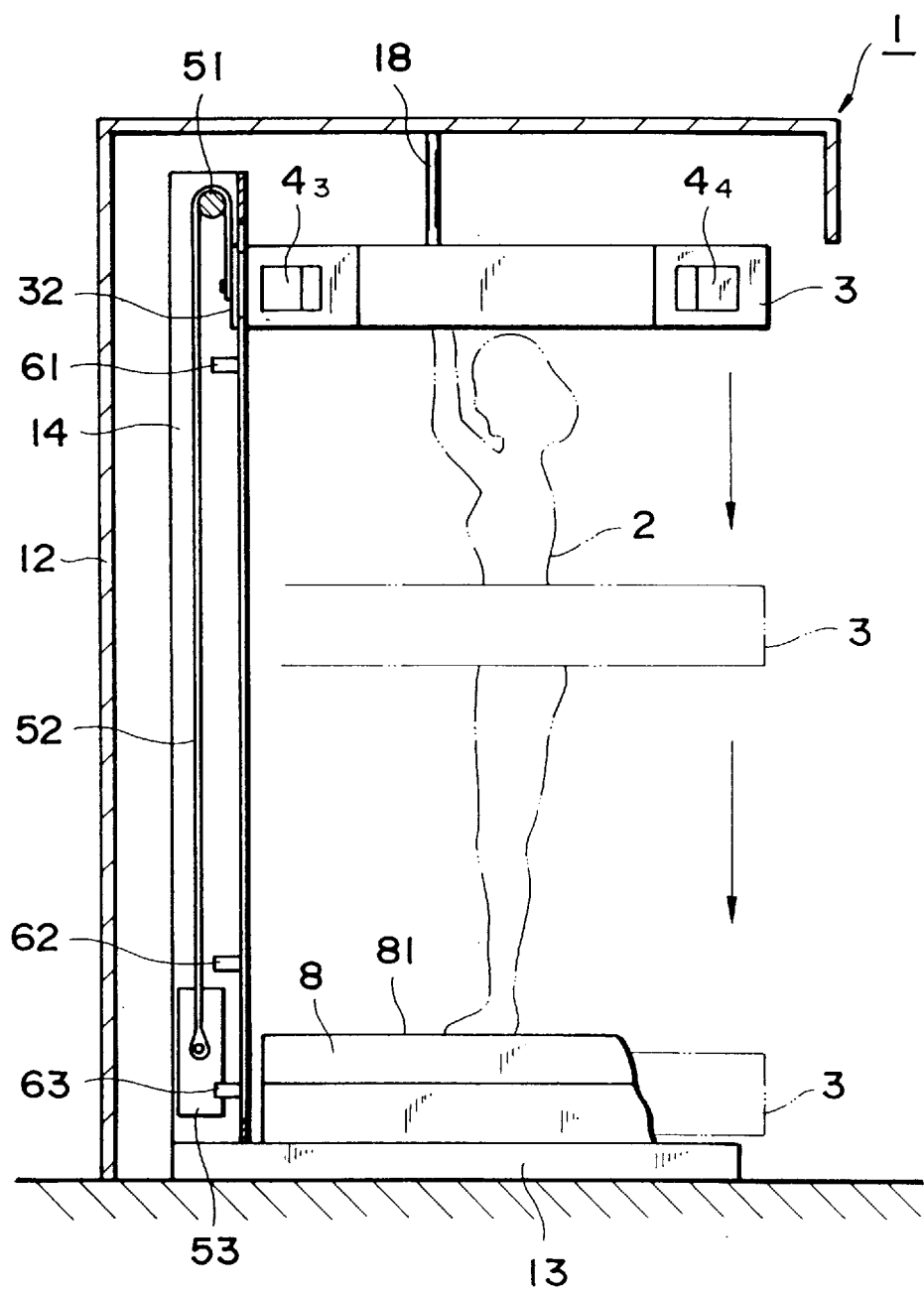
FIG. 7 is an explanatory drawing of a processing system of the three-dimensional shape measuring apparatus of FIG. 1.

Further, three limit switches 61 to 63 are attached to the column 14, as shown in FIG. 7. These limit switches 61 to 63 are for detecting positions of movement of the moving frame 3. The limit switches 61 to 63 are, for example, photoelectric switches. Each limit switch 61 to 63 is constructed so as to output an electric signal when the moving frame 3 moving along the column 14 passes before the limit switch 61 to 63. The limit switch 61 is mounted at a position where the moving frame 3 moving down from the uppermost part starts moving at uniform velocity, in the upper part of column 14. The limit switch 62 is mounted at a position lower than the lowermost position of measurement, in the lower part of column 14. The limit switch 63 is mounted at the lowermost part of the column 14.

Figure 8:
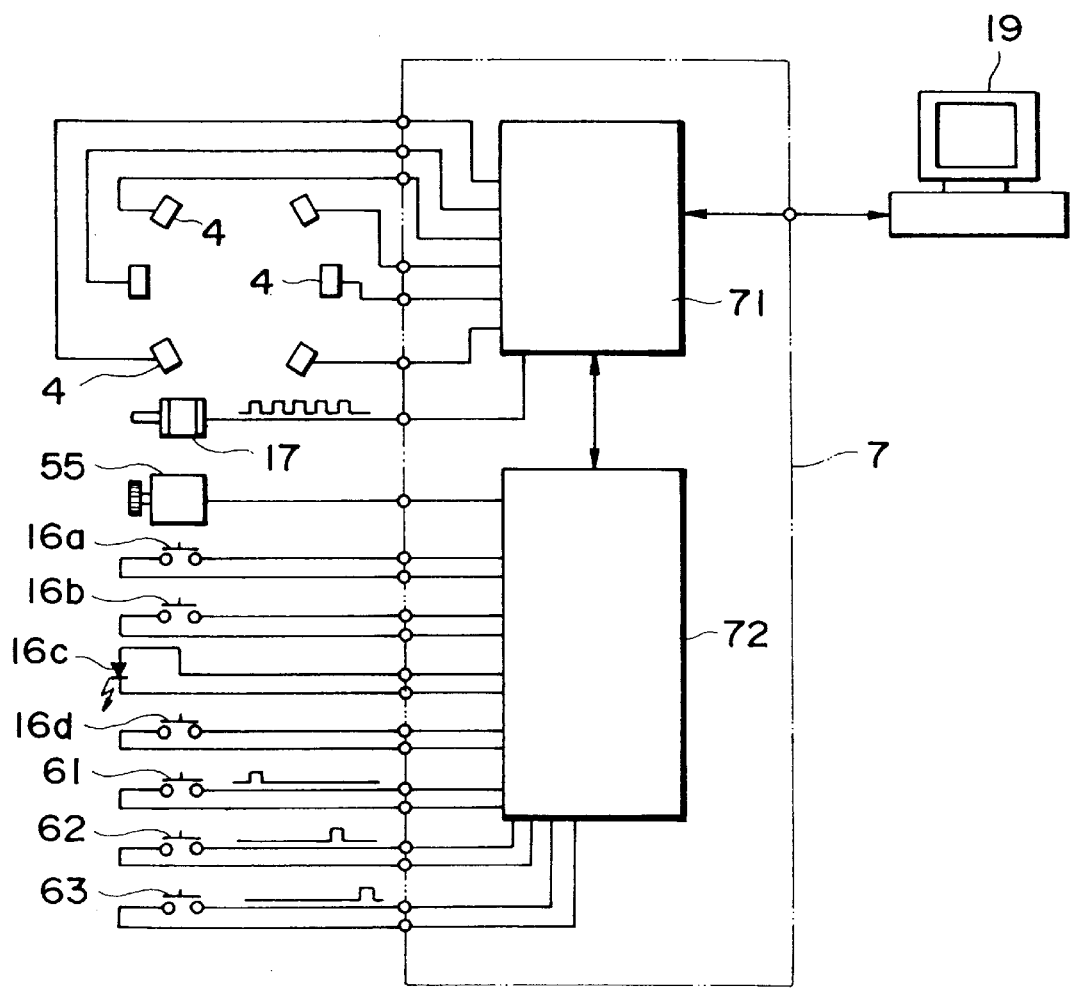
FIG. 8 is a block diagram of a control board and its peripheral devices in the apparatus of FIG. 1.

Again referring to FIG. 1, a control board 7 is installed on the base plate 13. The control board 7 is for controlling the drive of apparatus 1 and for analyzing the three-dimensional shape of the measured object 2 and is constructed to have signal processing circuit 71 and drive controlling circuit 72 as measuring means, as shown in FIG. 8. The signal processing circuit 71 is a circuit connected with each sensor 4, for calculating a distance to the surface of human body 2, based on an output signal from each sensor 4, and thereby measuring the three-dimensional shape of human body 2. The rotary encoder 17 is coupled with the signal processing circuit 71, so that the signal processing circuit 71 receives the pulse signal according to the movement of the moving frame 3. Since this signal processing circuit 71 can obtain a spatial position of each sensor 4 in accordance with a pulse output from the rotary encoder 17, each surface position of human body 2 can be obtained based on the distance data of each sensor 4, and based thereon, the three-dimensional shape of human body 2 is calculated. On the other hand, the drive controlling circuit 72 is a circuit coupled with the main power switch 16a, start-switch 16b, error display LED 16c, set switch 16d, and limit switches 61 to 63, for controlling the drive of motor 55 in accordance with a command signal or an output signal of each switch. The main power switch 16a, start switch 16b, error display LED 16c, and set switch 16d are disposed in the control panel 16 attached to the outer surface of the outer wall 12, as shown in FIG. 1. It is noted that FIG. 1 is illustrated as omitting illustration of wire cables etc. between the control board 7 and the respective portions.

Further, a placement stage 8 is located below the measurement space 11. This placement stage 8 is a stage for raising the measurement position of the human body 2 being measured. The placement stage 8 comprises a base surface 81 formed in a central top surface being raised in a step form. This base surface 81 is formed at a position being at least higher than the detection position of each sensor 4 when the moving frame 3 is located at the lowermost position. When the human body 2 is made to stand on this base surface 81, the human body 2 can be located within the moving range of the moving frame 3, in which the measurement can be carried out accurately down to the lower part of the human body 2, for example, to the ankle part thereof. By the arrangement wherein the base surface 81 is raised in the step form to be higher than the both side portions, positioning can be made securely in a front-to-back direction of the human body 2. Grips 18 are provided as being suspended from a ceiling surface. By making the human body 2 grasp the grips 18, positioning can be made reliably in a left-to-right direction of the human body 2. Further, a stool portion 82 is provided at a position lower than the base surface 81 in the front surface of the placement stage 8, so that the human body 2 can go into the measurement stage 11 easily by use of this stool portion 82.

Further, this placement stage 8 is a separate member from the base plate 13 as shown in FIG. 2 and is positioned between side pieces 13b, 13b of the base plate 13, but not on the base plate 13. Therefore, even if the human body 2 of heavy weight steps on the placement stage 8, distortion of the placement stage 8 due to the weight of human body 2 will not be transferred to the driving mechanism 5 and the moving frame 3. Accordingly, accurate measurement can be made without being influenced by such measurement distortion.

Further, the placement stage 8 is detachable from the measurement space 11. By attachment/detachment of the placement stage 8, the measurement of a tall human body 2 over the moving range of the moving frame 3 is possible. Specifically, in the state wherein the placement stage 8 is set in the measurement space (FIG. 1), the lower half of the human body 2 is measured with the human body 2 standing on the base surface 81. Thereafter, the placement stage 8 is removed from the measurement space 11 and the upper half of human body 2 is measured with the human body 2 standing in the measurement space 11 without the placement stage 8. Then the two data pieces of data (data piece of the upper half and data piece of lower half) are combined, thus measuring the total shape of human body 2.

As shown in FIG. 1 and FIG. 2, an internal wall cover 9 is set inside of the moving frame 3 (on the measurement space 11 side). The internal wall cover 9, which is placed along the internal surface of the moving frame 3, is a plate member for separating the moving space of the moving frame 3 from the measurement space 11. However, the internal wall cover 9 is not formed in the portion corresponding to the cutout portion 31 of the moving frame 3, so that the human body 2 can go into the measurement space 11 through that portion. The internal wall cover 9 prevents the human body 2 from touching the moving frame 3, while in motion, even if the human body 2 moves in the measurement space 11 during the measurement.

The internal wall cover 9 is provided with translucent windows 91 as shown in FIG. 2. The translucent windows 91 are made of a member having translucency to transmit the light emitted by the light emitting portion 41 of sensor 4, for example, a smoke acrylic plate, and they are provided in front of the corresponding sensors 4 and along the moving direction of the moving frame 3, i.e., along the vertical direction. Therefore, the internal wall cover 9 prevents the human body 2 from entering the moving space of the moving frame 3 and also permits projection of light from the sensors 4 to the human body 2 and reception of reflected light from the human body 2 by the sensors 4.

As shown in FIG. 2, angles formed by the internal faces of the internal wall cover 9 are determined to be angles such that when the light emitted from an arbitrary sensor 4 is reflected by the opposite internal face, reflected light thereof is not incident directly to the pertinent sensor 4. This arrangement of the angles prevents a distance to the opposite face from being erroneously detected.

Next, the method of use and the operation of the three-dimensional shape measuring apparatus 1 will be described.

In the apparatus shown in FIG. 1, the main power switch 16a is turned on to supply the power to each section of the three-dimensional shape measuring apparatus 1. Immediately after the main power switch 16a is turned on, a warm-up period of time of the apparatus 1 is set, such that other switches or the like cannot be activated. During the warm-up period, set switch 16d flashes (a light emitting device in the switch 16d is flashing) and after the warm-up period, the set switch 16d changes from the flashing state to a lighting state, which confirms completion of the warm-up of the apparatus 1.

When the set switch 16d is turned on after the warm-up period, the motor 55 is driven and the moving frame 3 moves up thereby. More specifically, when the set switch 16d is turned on, a drive signal is outputted from the drive controlling circuit 72 to the motor 55 as shown in FIG. 8, thereby driving the motor 55. The driving force of motor 55 is transmitted through the belt 54 to the roller 51 to rotate the roller 51, thereby lifting the moving frame 3 by the wire 52. On that occasion, a large amount of power is not needed to lift the moving frame 3 because the balancer 53, having a weight nearly equal to the moving frame 3, is suspended on the other end side of the wire 52. Owing to this, the power consumed by the motor 55 is small. Since the moving frame 3 is lifted naturally, without strain, the movement of the moving frame 3 is smooth. When the moving frame 3 is already moved up after the warm-up period, the moving frame 3 is prevented from moving even with the set switch 16d on.

In FIG. 1, after the moving frame 3 is moved up, the human body 2 being measured is made to go into the measurement space 11. In the measurement space 11 the human body 2 stands on the base surface 81 of the placement stage 8 and grasps the grips 18, thereby keeping the human body 2 in a state suitable for measurement. It is also permissible to locate the human body 2 there, prior to the above-stated upward setting of the moving frame 3 or during the setting.

Next, the start switch 16b is turned on. Then the motor 55, receiving a command signal from the drive controlling circuit 72, is driven and the driving force of motor 55 is transmitted through the belt 54, roller 51, and wire 52 to the moving frame 3, whereby the moving frame 3 moves down from the upper part of apparatus 1 as shown in FIG. 7. When the moving frame 3 passes by the limit switch 61, a measurement start signal is outputted from the limit switch 61 to the drive controlling circuit 72 in FIG. 8 and the measurement start signal is supplied through the drive controlling circuit 72 to the signal processing circuit 71. When the signal processing circuit 71 receives the measurement start signal, the signal processing circuit 71 starts counting pulses outputted from the rotary encoder 17, and the signal processing circuit 71 successively counts the intermittent pulses with the downward movement of the moving frame 3.

For example, the rotary encoder 17 is arranged to output a pulse every 5-mm of movement of the moving frame 3, whereby vertical positions (position information) of the moving frame 3 can be determined by counting the pulses. Each sensor 4 is operated in synchronism with the pulse signal. Specifically, the signal processing circuit 71 outputs an operation command signal to each sensor 4 for every input of pulse from the rotary encoder 17. As a result, as shown in FIG. 2, the light emitting elements 41b of the light emitting portion 41 of each sensor 4 successively emit the light to project the light (beams 41a) toward the human body 2 being measured. Namely, a horizontal scan of light is effected by the sensors 4. Then the light receiving elements 42 of each sensor 4 receive scattered light (reflected light) by the surface of the human body 2 upon irradiation of the human body 2, whereby electric signals (distance detection signals) corresponding to distances from the sensors 4 to the surface of human body 2 are outputted based on Eq. (3) described previously to be supplied to the signal processing circuit 71. This operation of sensors 4 is repeated for every pulse input from the rotary encoder 17.

For example, supposing the measurement range in the vertical direction (the effective moving range of the moving frame 3) is 170 cm, the rotary encoder 17 intermittently outputs 341 pulses in one measurement, so that totally 341 distance data pieces to the surface of human body 2 are obtained at positions of vertical intervals of 5 mm for every light emitting portion 41b.

The scanning of beams 41a by the light emitting portions 41 of sensors 4 is not limited to the plural light emitting elements 41b, but other techniques may be adopted; for example, a scanning method with a rotary prism or a rotary mirror disposed on the optic axis to deflect a beam 41a emitted from a single light emitting device. Further, the sensors 4 may be any other detecting means than the aforementioned reflection-type photoelectric sensors as long as they can measure distances to the human body 2.

Since the sensors 4 are located as shown in FIG. 6, irradiation light from any one sensor 4 reaches the portions hindered by the human body 2 itself, such as the portions below the armpit part and below the crotch part, so that accurate measurement can be made for such portions. Accordingly, accurate measurement of the three-dimensional shape of human body 2 can be carried out.

Figure 9:
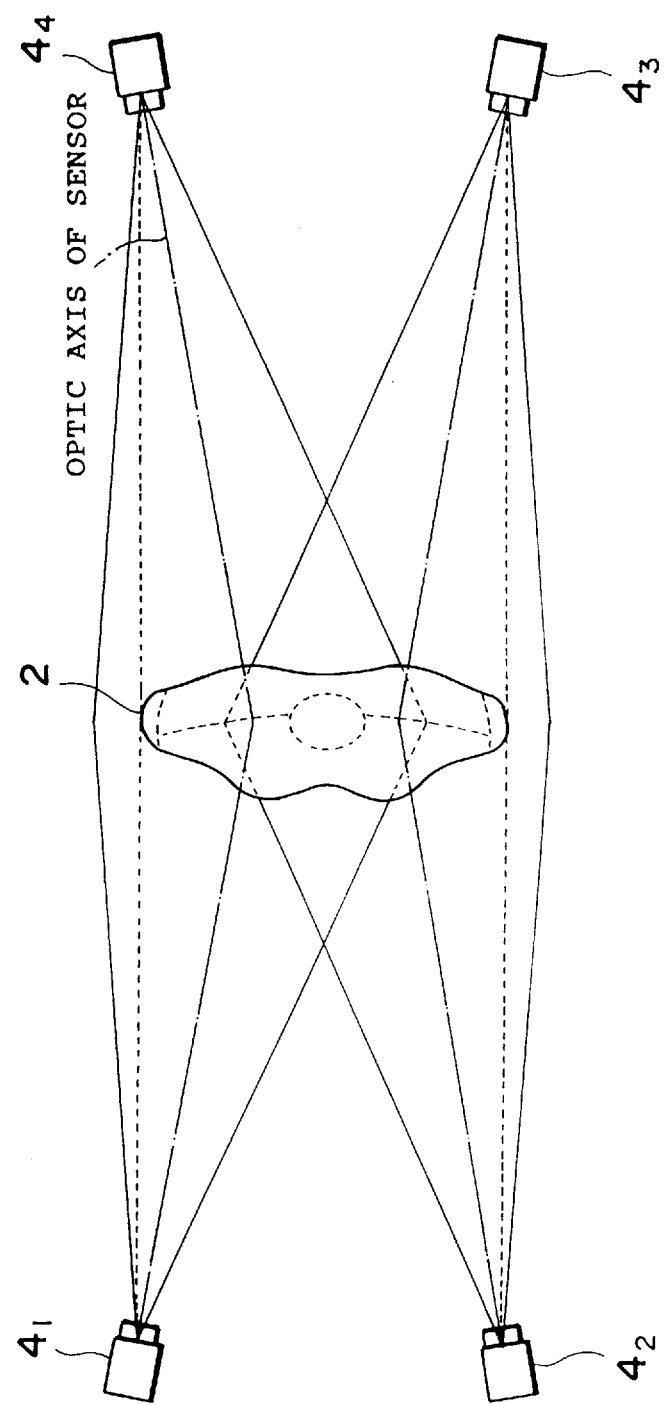
FIG. 9 to FIG. 11 are drawings to show several examples of preferred locations of sensors in the three-dimensional apparatus of FIG. 1, wherein the respective figures show examples wherein the number of sensors is 6, 4, 5, or 8.
Figure 10:
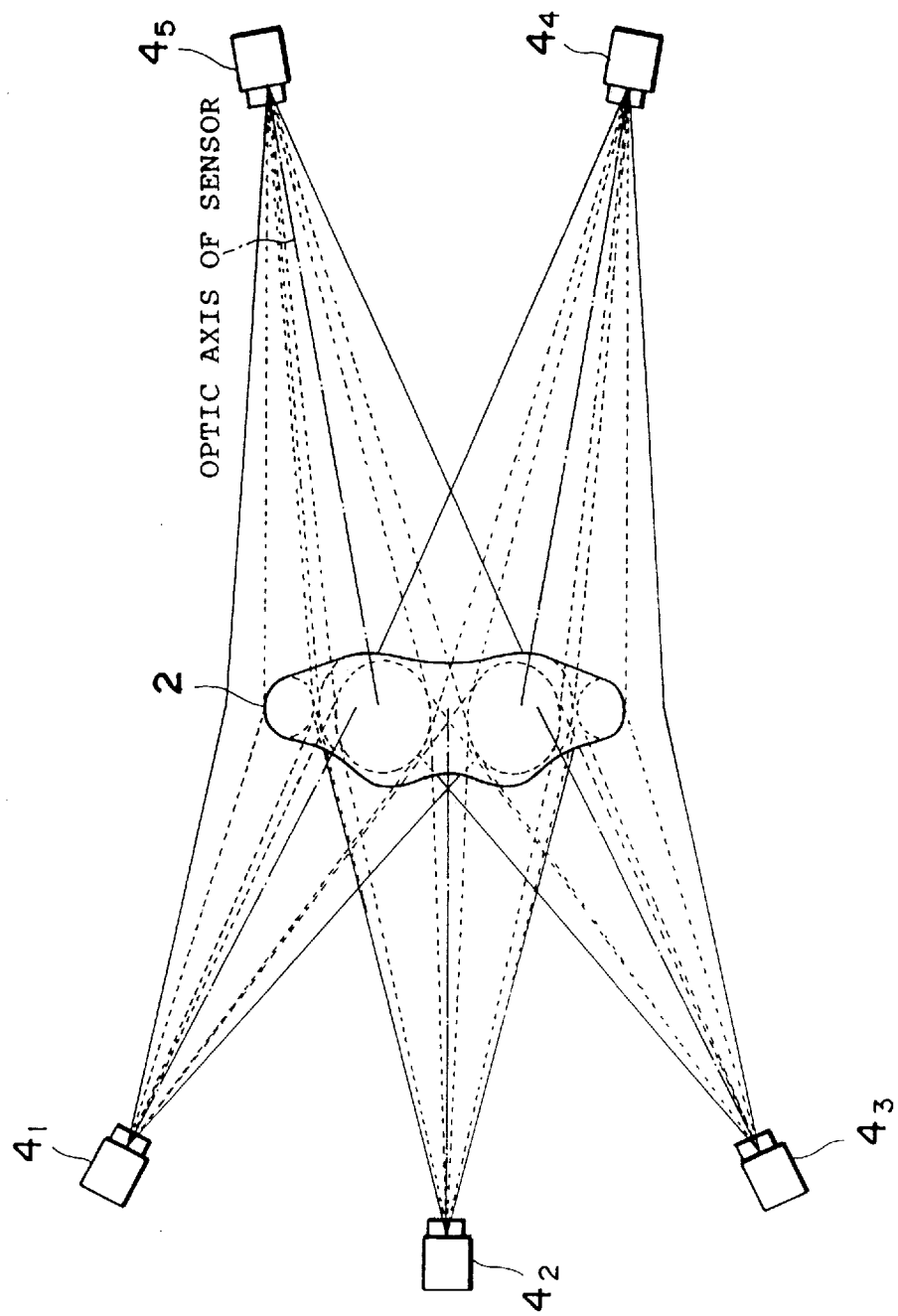
Figure 11:
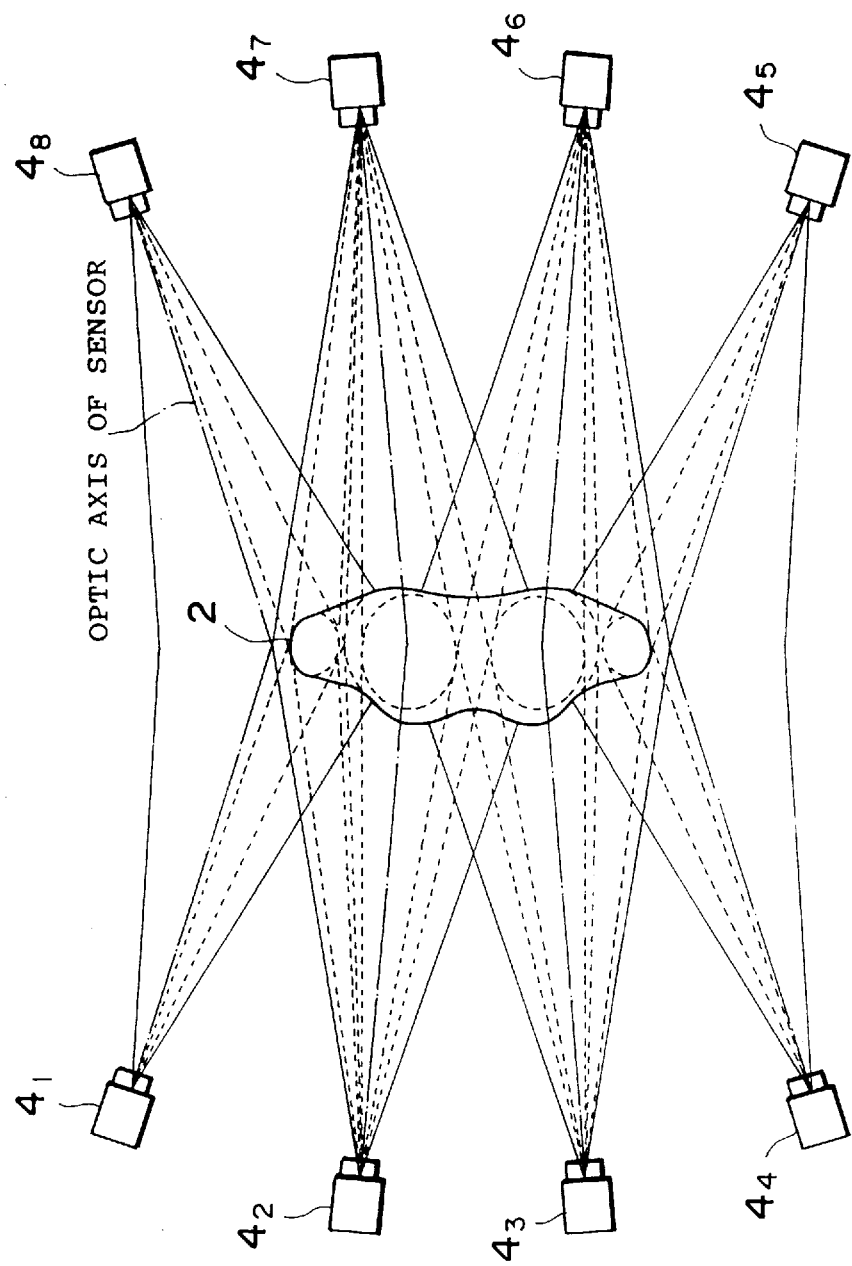

FIG. 9 to FIG. 11 show preferred arrangement examples wherein the number of the sensors 4 is 4, 5, or 8. In the case of the arrangement of four sensors 4 shown in FIG. 9, two sensors $4_1$, $4_2$ ($4_3$, $4_4$) are located at both extremes of a narrow angular range of about 32° on either the front side or the back side of human body 2 and the optic axes of the respective sensors $4_1$, $4_2$ ($4_3$, $4_4$) intersect approximately 467 mm away from the center of the measurement space. When there are five sensors 4, as shown in FIG. 10, locations of three sensors $4_1$ to $4_3$ on the front side are the same as those of the sensors $4_1$ to $4_3$ shown in FIG. 6 and locations of two sensors $4_4$, $4_5$ on the back side are the same as those of the sensors $4_3$, $4_4$ shown in FIG. 9. When there are eight sensors, as shown in FIG. 11, four sensors are located almost equally within an angular range of about 70° on either the front side or the back side. The optic axes of the sensors $4_1$, $4_4$ ($4_5$, $4_8$) at both extremes, intersect approximately 710 mm away from the center of the measurement space and the optic axes of the inside sensors $4_2$, $4_3$ ($4_6$, $4_7$) intersect approximately 900 mm away from the center of the measurement space. In either case, since the sensors 4 are located so as to face the front and the back of human body, accurate measurement can be made for the portions below the armpit portion and the crotch portion in the same manner as in the arrangement example of six sensors shown in FIG. 6.

Figure 12:
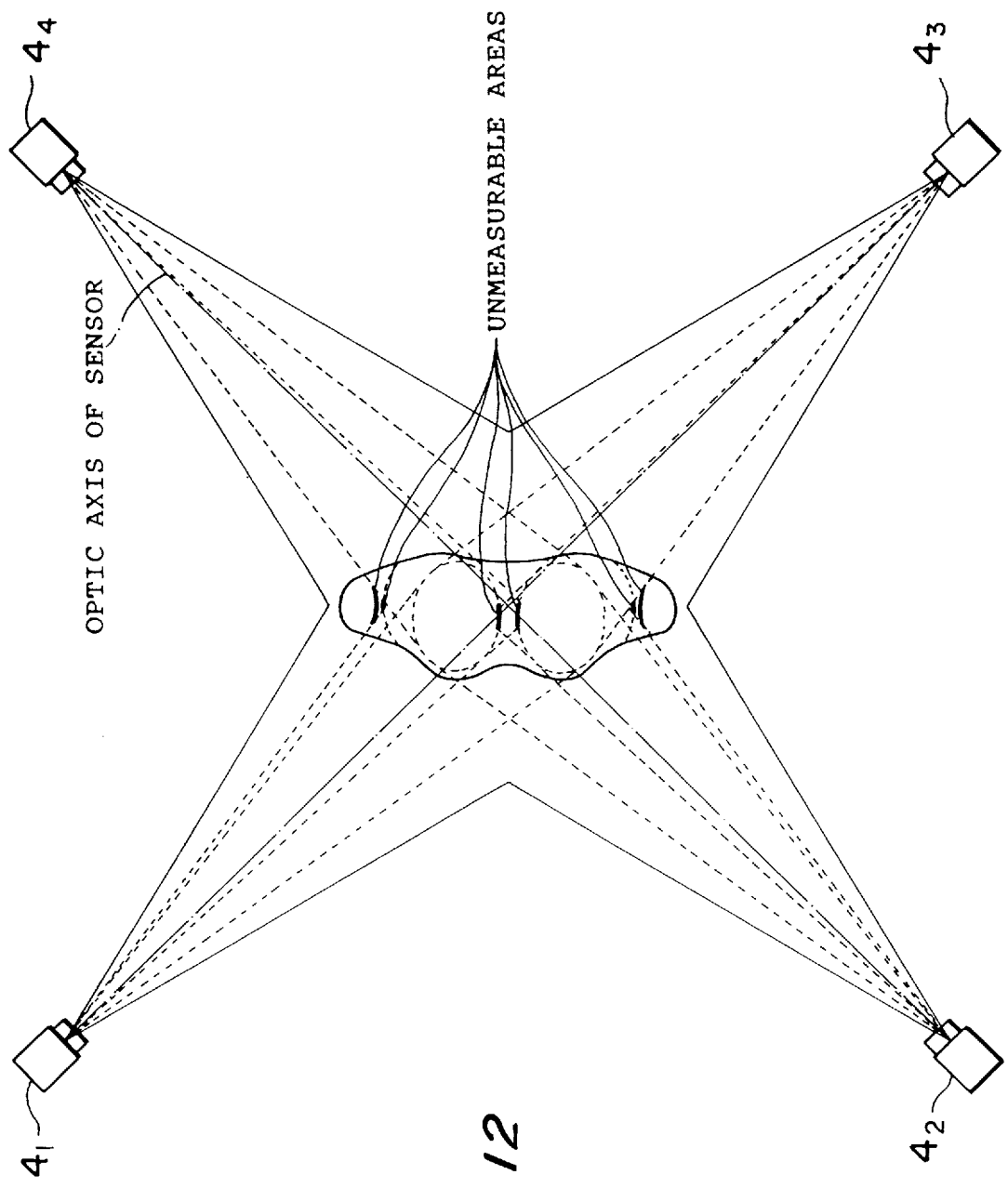
FIG. 12 is a drawing to show an unpreferred location example in which four sensors are arranged in the three-dimensional apparatus of FIG. 1, for comparison with the examples of FIGS. 9 to 11.
Figure 13A:
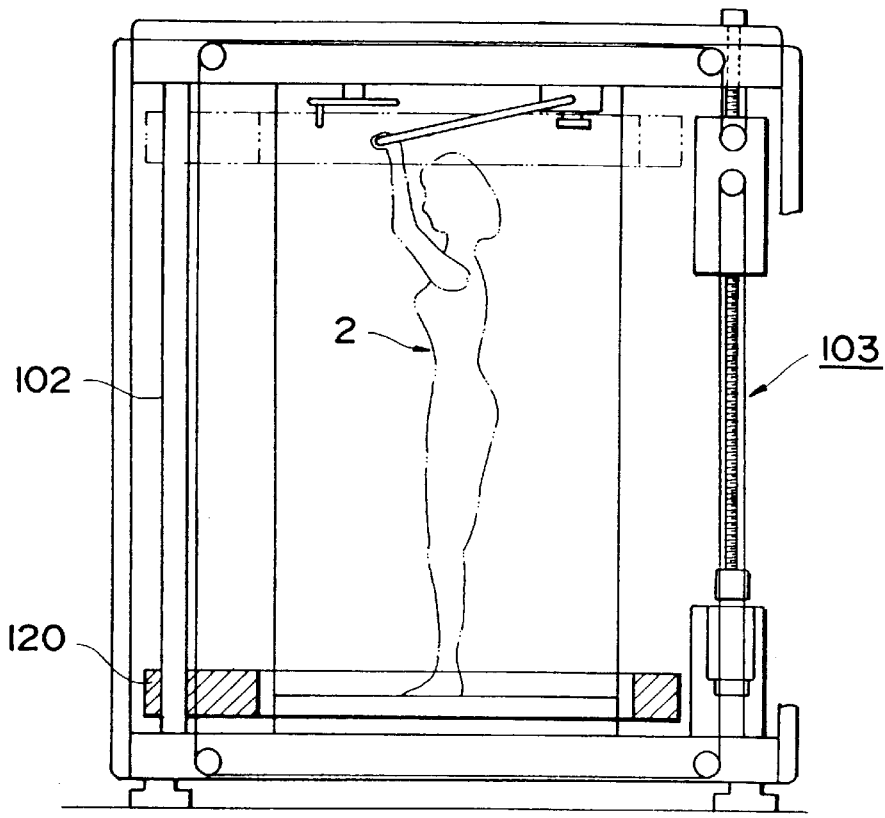
FIG. 13A and FIG. 13B are structural drawings of the conventional three-dimensional shape measuring apparatus.
Figure 13B:
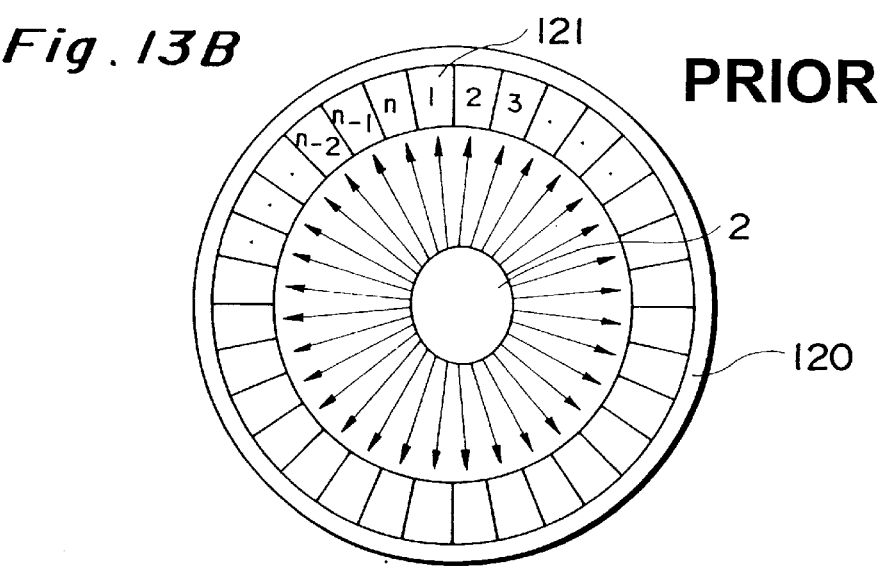

For the sake of comparison, an example is described having four sensors 4 located at equal distances and at equal intervals from the center of human body 2, as shown in FIG. 12. In this case, the irradiation light from the sensors 4 is interrupted by the arm, the leg, the trunk, or the like, thereby failing to reach surfaces of opposite portions below the armpit portion and below the crotch portion. Thus, surface positions of such portions could not be measured and accurate measurement of the surface shape was not possible.

To overcome this, a possible method is to enlarge the scanning range with an increased number of sensors 4. However, this method has problems, such as an increase in wasteful measurement because of redundant measurement positions, an increase in cost, an increase in scattered light due to the increased number of sensors, and an increase in adjustment complexity. In contrast, the arrangement of sensors 4 shown in FIG. 9 permits accurate measurement for the portions below the armpit part and below the crotch part by using a smaller number of (four) sensors 4.

To locate the sensors 4 so as to face the human body 2 in order to accurately measure the portions below the armpit and below the crotch of human body 2, as described, a preferred arrangement is such, that the sensors 4 are concentrated within a predetermined area. Of course, in order to assure measurement of a side face, an additional sensor may be provided outside this area.

The description of the operation of the apparatus of the present embodiment will continue with reference to FIG. 2. During this measurement the moving frame 3 continuously moves down along the measurement space 11. Even if the human body 2 moves for some reason, there is no chance that the human body 2 will come into contact with the moving frame 3 because the internal wall cover 9 separates the measurement space 11 from the moving space of the moving frame 3. Accordingly, in that case the human body 2 is prevented from touching the moving frame 3 and thereby being injured, and the moving frame 3, the driving mechanism 5, and so on are prevented from being damaged, which assures very safe operation.

Then the distance detection signals from sensors 4 to the human body 2, obtained during the downward movement of the moving frame 3, are sent to the signal processing circuit 71 to be processed together with the spatial positions of the sensors 4, based on the aforementioned position information of the moving frame 3, thereby being converted into spatial position information of a surface of the human body 2. By combination of this spatial position information, the stereoscopic, three-dimensional shape of the human body 2 can be obtained.

When the moving frame 3 passes the limit switch 62 as shown in FIG. 7, the drive controlling circuit 72 decreases the descending velocity of the moving frame 3, so that the moving frame 3 stops soon after the moving frame 3 passes the limit switch 63. At this time, since the placement stage 8 keeps the placement position of human body 2 elevated, the stop position of the moving frame 3 is lower than the placement position of human body 2 (the base surface 81). Therefore, the measurement can be done completely down to the foot part of the human body 2 with movement of the moving frame 3. When the moving frame 3 stops midway for some reason or when the apparatus fails to obtain the shape data in the desired range, the error display LED 16c is turned on, whereby an anomaly of the apparatus 1 can be recognized readily. In that case, the set switch 16d is turned on to restart the measurement.

When monitor 19 is connected to the signal processing circuit 71 as shown in FIG. 8, the three-dimensional shape of human body 2 will be displayed as a stereoscopic image by computer graphics or the like, which facilitates obtaining the shape. At the same time, dimensions can also be displayed by numerical values based on numerical processing from the surface shape.

Next described are the use method of the three-dimensional shape measuring apparatus 1 and the operation thereof where the human body 2 to be measured is tall.

In FIG. 1, first, the main power switch 16a is turned on to supply the power to each section of the three-dimensional shape measuring apparatus 1 in the same manner as described previously. Then the set switch 16d is turned on after the lapse of the warm-up period, thereby moving the moving frame 3 upward. After the moving frame 3 is moved up, the human body 2 to be measured is then made to go into the measurement space 11. In the measurement space 11 the human body 2 is made to stand on the base surface 81 of the placement stage 8 and to grasp the grips 18, thereby keeping the human body 2 in a state suitable for the measurement. The placement of the human body 2 may be carried out prior to the foregoing setting of the moving frame 3 in the up position or during the setting.

Then the start switch 16b is turned on to carry out the measurement of three-dimensional shape of the human body 2 in the same manner as described previously. At this time, data of the three-dimensional shape of the upper part of the human body 2 is not obtained, i.e., the three-dimensional shape of the head and the upper half of the body, because the human body 2 is tall.

Next, the initial measurement is carried out and thereafter the set switch 16d is again turned on to bring the apparatus 1 into the state ready for measurement. Before or after turning on the set switch, the placement stage 8, having been set in the measurement space 11, is removed. Then the human body 2 is made to go into the measurement space 11. At this time, the human body 2 will be located at a position lower than a position during the initial measurement by the height of the placement stage 8. In this state the start switch 16b is turned on to carry out the measurement of the three-dimensional shape of the head and the upper half of the human body 2.

After completion of the two measurements (the measurement of the lower half part and the measurement of the upper half part), the signal processing circuit 71 searches for a redundant data part in each measurement data and combines the measurement data with an overlap of the redundant data.

In this way, the two measurements and a combination of the respective data allow accurate measurement of the total three-dimensional shape even if the human body 2 has a height taller than the measurement range of apparatus 1 (the moving range of the moving frame 3).

As described above, since the three-dimensional shape measuring apparatus 1 of the present embodiment is arranged so that the sensors 4 for horizontal scanning are arranged in the two groups opposite to each other, accurate measurement is also possible for the recessed portions in the surface of the human body 2, such as the portions below the armpit and below the crotch. Especially, by the arrangement wherein each sensor is installed at a height different from those of the opposite sensors, the output light from the opposite sensors is prevented from directly entering the associated sensor, thereby preventing generation of noise. Further, the U-shape or horseshoe shape of the moving frame facilitates introduction of the human body 2 into the measurement space. The provision of the placement stage 8 permits certain measurement of the three-dimensional shape of the lower part of human body 2 being measured. Further, the separate arrangement of the placement stage 8 from the moving frame 3, the driving mechanism 5, etc. enables accurate measurement. The detachable arrangement of the placement stage 8 permits reliable measurement of the total three-dimensional shape even for the tall human body 2. In addition, the provision of the internal wall cover 9 assures safe measurement. Further, the provision of the balancer 53 in the driving mechanism 5 enhances the movement efficiency of the moving frame 3, thereby decreasing the consumption power of the apparatus 1.

The three-dimensional shape measuring apparatus 1 of the present embodiment was described as an apparatus for measuring the three-dimensional shape of the human body 2, but the measured object is not limited to the human body 2. It is also possible to measure other objects.

The three-dimensional shape measuring apparatus of the present embodiment was arranged to perform the measurement of a three-dimensional shape while moving in the direction of height, but the measurement direction is not limited to this. It is also possible to perform the measurement while the sensors are located on the moving frame moving in a direction of an arbitrary axis, for example, in the horizontal direction.

Although the above description concerned the embodiment wherein the sensors were positioned as concentrated on the two opposite sides of the moving frame, the arrangement of sensors is not limited to this. For reliable measurement of the shape of projections and depressions in the surface of a measured object, it is, however, necessary that the optic axes of the respective sensors (in the case of the arrangement having the scanning angle, the center lines thereof) not intersect at one point (in a case in which respective sensors have different axial locations, lines on a projection surface in the axial direction do not intersect at one point). After the sensors are located as described, the measured object is placed so that each projection and depression in the surface are directed to either sensor, and then the measurement is carried out, whereby the shape of the projections and the depressions in the surface can be measured accurately. From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Applications No. 8-228632 (228632/1996) filed on Aug. 29, 1996 and No. 9-184043 (184043/1997) filed on Jul. 9, 1997 are hereby incorporated by reference.

What is claimed is:

1. A three-dimensional scanning apparatus for detecting a three-dimensional shape of an object placed in a measurement space in a non-contact manner, comprising:

a moving frame disposed around said measurement space so as to surround a predetermined axis passing through a center of said measurement space, said moving frame arranged to be movable in a direction of said predetermined axis;

at least four sensors for measuring distances to surfaces of different portions of said object, said sensors being positioned along a circumferential direction on said moving frame so that a plurality of said at least four sensors are located mainly in each predetermined region on two opposite sides of said moving frame, each of said at least four sensors measures a distance to said object by detecting scattered or reflected light from said object;

a driving mechanism for moving said moving frame in a direction of said predetermined axis;

a position detector for detecting and outputting a position of said moving frame in the direction of said axis; and an analyzer for calculating data of said distance from each of said at least four sensors to a surface of said object at each moving position of said moving frame, based on outputs from each of said at least four sensors and said position detector, and for analyzing a three-dimensional shape of the surface of said object, based on the data of said distances wherein optic axes of respective ones of said at least four sensors intersect at different points on a projection surface.

2. A three-dimensional scanning apparatus according to claim 1, wherein said at least four sensors detect distances to the object by triangulation, each of said at least four sensors having a light projecting portion for projecting light toward the object and a light receiving portion, disposed a predetermined distance apart from said light projecting portion for receiving said scattered or said reflected light from the object, wherein said light projecting portion effects scanning of light within a predetermined angle in a direction perpendicular to the direction of said axis.

3. A three-dimensional scanning apparatus according to claim 2, wherein scanning centers of said respective light projecting portions in ones of said at least four sensors disposed adjacent to each other on a same side of said moving frame intersect with others of said ones of said at least four sensors at a point being more distant from said respective ones of said at least four sensors than a center of said measurement space.

4. A three-dimensional scanning apparatus according to claim 2, wherein the light receiving portion of said each of said at least four sensors is disposed a predetermined distance apart, in the direction of said axis, from said light projecting portions of others of said at least four sensors being disposed opposite thereto.

5. A three-dimensional scanning apparatus according to claim 2, further comprising an internal wall cover separating said measurement space from a moving space of said moving frame, said internal wall cover having a plurality of windows for transmitting light in portions between said at least four sensors and said object.

6. A three-dimensional scanning apparatus according to claim 1, further comprising a placement stage, on which said object is placed, in said measurement space.

7. A three-dimensional scanning apparatus according to claim 1, further comprising an internal wall cover separating said measurement space from a moving space of said moving frame.

8. A three-dimensional scanning apparatus according to claim 1, wherein said moving frame has a U-shape.

9. A three-dimensional scanning apparatus according to claim 1, wherein the direction of said axis is substantially a direction of gravity, said three-dimensional scanning apparatus further comprising a rotating member disposed above said measurement space, and a flexible elongated member connected at one end thereof to said moving frame and at another end thereof to a balancer having a substantially same weight as the moving frame, said flexible elongated member being hooked around said rotating member, wherein said driving mechanism rotates said rotating member to move said flexible elongated member and thereby move said moving frame.

10. A three-dimensional scanning apparatus according to claim 1, wherein said moving frame has a horseshoe shape.

11. A three-dimensional scanning apparatus for detecting a three-dimensional shape of an object placed in a measurement space in a non-contact manner, comprising:

a moving frame disposed around said measurement space so as to surround a predetermined axis passing through a center of said measurement space, said moving frame arranged to be movable in a direction of said predetermined axis;

a plurality of sensors positioned along a circumferential direction on said moving frame, for measuring distances to surfaces of different portions of said object, each of said plurality of sensors measures said distances to said surfaces of said different portions of said object by detecting scattered or reflected light from said object;

a driving mechanism for moving said moving frame in a direction of said predetermined axis;

a position detector for detecting and outputting a position of said-moving frame in the direction of said axis; and an analyzer for calculating data of said distance from each of said sensors to a surface of said object at each moving position of said moving frame, based on outputs from said each of said sensors and said position detector, and for analyzing a three-dimensional shape of the surface of said object, based on the data of said distance, wherein optic axes of said respective ones of said sensors intersect at different points on a projection surface.

12. A three-dimensional scanning apparatus according to claim 11, wherein said sensors detect distances to the object by triangulation, each of said sensors having a light projecting portion for projecting light toward the object and a light receiving portion, disposed a predetermined distance apart from said light projecting portion, for receiving said scattered or said reflected light from the object, wherein said light projecting portion effects scanning of light within a predetermined angle in a direction perpendicular to the direction of said axis.

13. A three-dimensional scanning apparatus according to claim 12, wherein scanning centers of said respective light projecting portions in ones of said sensors disposed adjacent to each other on a same side of said moving frame intersect with others of said ones of said sensors at a point being more distant from said respective ones of said sensors than a center of said measurement space.

14. A three-dimensional scanning apparatus according to claim 12, wherein the light receiving portion of said each of said sensors is disposed a predetermined distance apart, in the direction of said axis, from said light projecting portions of others of said sensors being disposed opposite thereto.

15. A three-dimensional scanning apparatus according to claim 12, further comprising an internal wall cover separating said measurement space from a moving space of said moving frame, said internal wall cover having a plurality of windows for transmitting light in portions between said sensors and said object.

16. A three-dimensional scanning apparatus according to claim 11, wherein said moving frame has a U shape.

17. A three-dimensional scanning apparatus according to claim 11, further comprising a placement stage, on which said object is placed, in said measurement space.

18. A three-dimensional scanning apparatus according to claim 11, further comprising an internal wall cover separating said measurement space from a moving space of said moving frame.

19. A three-dimensional scanning apparatus according to claim 11, wherein the direction of said axis is substantially a direction of gravity, said three-dimensional scanning apparatus further comprising a rotating member disposed above said measurement space, and a flexible elongated member connected at one end thereof to said moving frame and at another end thereof to a balancer having a substantially same weight as the moving frame, said flexible elongated member being hooked around said rotating member, wherein said driving mechanism rotates said rotating member to move said flexible elongated member and thereby move said moving frame.

20. A three-dimensional scanning apparatus according to claim 11, wherein said moving frame has a horseshoe shape.

* * * * *

UNITED STATES PATENT AND TRADEMARK OFFICE
CERTIFICATE OF CORRECTION

PATENT NO. : 5,850,290
DATED : December 15, 1998
INVENTOR(S) : HORIGUCHI et al.

It is certified that error appears in the above-identified patent and that said Letters Patent is hereby corrected as shown below:

ON THE COVER PAGE:

Please add ,Item:

-- [30] Foreign Application Priority Data

Aug. 29, 1996  [JP]   Japan    8-228632

July 9, 1997   [JP]   Japan    9-184043 --

Signed and Sealed this

Twenty-ninth Day of June, 1999

Attest:

Attesting Officer

Q. TODD DICKINSON

Acting Commissioner of Patents and Trademarks